United States Patent
Sobolev et al.

(10) Patent No.: US 10,209,131 B2
(45) Date of Patent: Feb. 19, 2019

(54) AUTOMATED DELAY LINE ALIGNMENT

(71) Applicant: Ultrafast Systems LLC, Sarasota, FL (US)

(72) Inventors: Alexander Sobolev, Sarasota, FL (US); Nikita Kurakin, Sarasota, FL (US); Alexey Gusev, Sarasota, FL (US)

(73) Assignee: ULTRAFAST SYSTEMS LLC, Sarasota, FL (US)

( * ) Notice: Subject to any disclaimer, the term of this patent is extended or adjusted under 35 U.S.C. 154(b) by 0 days.

(21) Appl. No.: 15/753,459

(22) PCT Filed: Aug. 19, 2016

(86) PCT No.: PCT/US2016/047838
§ 371 (c)(1),
(2) Date: Feb. 19, 2018

(87) PCT Pub. No.: WO2017/035005
PCT Pub. Date: Mar. 2, 2017

(65) Prior Publication Data
US 2018/0245977 A1    Aug. 30, 2018

Related U.S. Application Data (60) Provisional application No. 62/208,546, filed on Aug. 21, 2015.

(51) Int. Cl.
*G01J 3/02*         (2006.01)
*G01J 1/42*         (2006.01)
(Continued)

(52) U.S. Cl.
CPC .......... *G01J 3/0289* (2013.01); *G01B 11/272* (2013.01); *G01J 1/30* (2013.01);
(Continued)

(58) Field of Classification Search
CPC ..... G01J 3/0289; G01J 3/0291; G01B 11/272; G01N 21/636
See application file for complete search history.

(56) References Cited

U.S. PATENT DOCUMENTS 4,866,362 A * 9/1989 Parker .................... B25J 19/022
                                                 700/259
4,867,560 A * 9/1989 Kunitsugu ............. B23K 26/04
                                                 356/139.05
(Continued)

OTHER PUBLICATIONS

Ironside et al. "A self-aligning scanning optical delay line" Journal of Physics E. Scientific Instruments, IOP Publishing, Bristol, GB, vol. 17, No. 6, pp. 440-441, XP020017383, ISSN: 0022-3735, DOI: 10.1088/0022-3735/17/6/003 Jun. 1, 1984.

*Primary Examiner* — Maurice Smith
(74) *Attorney, Agent, or Firm* — Husch Blackwell LLP (57) ABSTRACT

A system and method for aligning a light beam in a spectroscopic measuring device such as a pump-probe device is provided. The system and method comprise a first motorized mirror (66b) positioned to receive and transmit a light beam (60a); a second motorized mirror (66c) positioned relative to the first mirror to receive the light beam from the first mirror and transmit the light beam to a delay line (64); a third mirror (78) positioned to receive the light beam from the delay line and transmit said light beam to a detector (80); and a computer-based processor (82) in communication with the detector and the first and second mirrors, the processor configured to a) receive and process data relating to the light beam from the detector, and b) cause movement of the first and second mirrors to change an angle of the mirrors based on the data relating to the light beam.

14 Claims, 4 Drawing Sheets

(51) Int. Cl.
*G01B 11/27* (2006.01)
*G01J 1/30* (2006.01)
*G01N 21/63* (2006.01)

(52) U.S. Cl.
CPC .......... *G01J 1/4257* (2013.01); *G01J 3/0291* (2013.01); *G01J 3/0297* (2013.01); *G01N 21/636* (2013.01)

(56) References Cited

U.S. PATENT DOCUMENTS

| | | | | |
|---|---|---|---|---|
| 5,536,916 | A * | 7/1996 | Kohari | B23K 26/043 219/121.74 |
| 8,724,111 | B2 * | 5/2014 | Gusev | G01N 21/59 356/432 |
| 2004/0030519 | A1 * | 2/2004 | Messina | G01B 11/272 702/94 |
| 2004/0056010 | A1 * | 3/2004 | Ho | G01B 11/272 219/121.78 |
| 2007/0020785 | A1 | 1/2007 | Bruland et al. | |
| 2013/0088709 | A1 * | 4/2013 | Koenig | G02B 21/0028 356/72 |

* cited by examiner

AUTOMATED DELAY LINE ALIGNMENT

FIELD OF THE INVENTION

Embodiments of this invention relate to a system and methods for aligning an optical delay line in an optically gated (pump-probe) spectrometer to maintain the initial beam pointing after the delay line over the course of a pump-probe measurement steps.

BACKGROUND OF THE INVENTION

Optically gated spectroscopy methods (pump-probe transient absorption, fluorescence upconversion, etc.) are widely used to study fast photo-induced processes (e.g., chemical reactions, etc.). In a pump-probe setup, a laser beam is split into a pump pulse and a temporary delayed probe pulse. In general, a sample is irradiated with a laser pump pulse, which generates an excitation (or other perturbation) in the sample. Then, after an adjustable time delay and while the excited state is being relaxed, a laser probe pulse is sent to the sample. The time delay is typically controlled with an optical delay line. By analyzing the intensity of the light from the probe pulse, the transmission or reflectance of the sample is measured. This is repeated over a series of pump-probe delays to measure the photo-induced changes in in the sample over time after the periodic excitation by the pump pulse.

An optical delay line generally works by precisely controlling the position of a retroreflector. In a retroreflector, a light beam is reflected back along a vector that is parallel to but opposite the direction from the beam's source. Any change in the position of the retroreflector will affect the path length that the light beam has to travel before arriving at the sample. One can calculate how much the laser pulse is delayed in time with each change in the position of the retroreflector based on the speed of light. By monitoring the probe pulse as a function of the time delay, information can be obtained on the decay of the generated excitation or on other processes initiated by the pump pulse.

Figure 1:
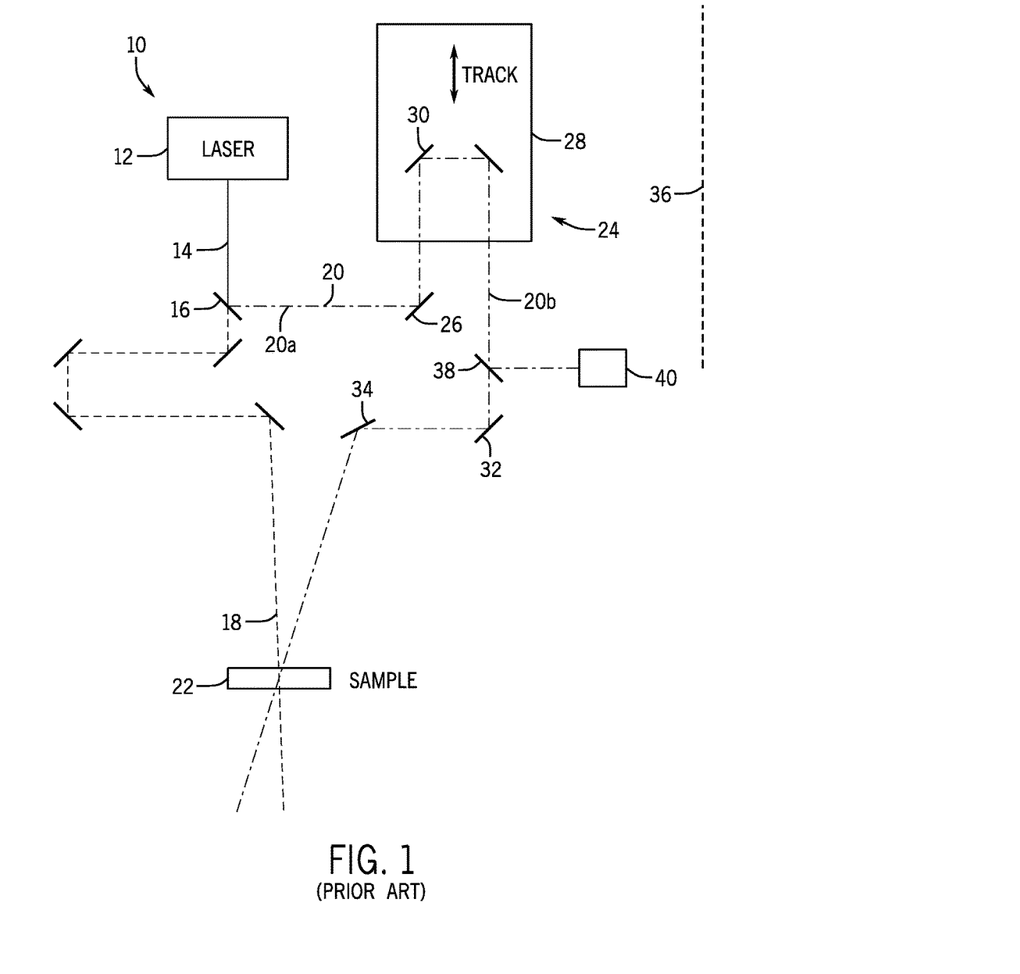
FIG. 1 is a depiction of an embodiment of a conventional pump probe arrangement.

FIG. 1 illustrates an embodiment of a conventional pump-probe arrangement. As illustrated, the pump-probe device 10 includes a laser source 12 which generates a laser beam 14, and a semitransparent beam splitter 16 which splits the laser beam 14 into a pump pulse beam 18 and a probe pulse beam 20. The two beams follow different optical paths but are spatially overlapped in the sample 22. The pump pulse beam 18 is directed via a series of mirrors to the sample 22, and the incoming probe pulse beam 20a is directed to a variable (motorized) optical delay line 24. The optical delay line 24 is a reflective device which includes a retroreflector assembly 30 mounted on a motorized translation stage 28, which is moved along a track (arrow ↔). Over the course of the measurement period, the translation stage 28 and retroreflector 30 is translated along the track in order to modify the length of the beam path of the probe pulse beam 20 relative to the length of the pump pulse beam 18, thus delaying the delivery of the probe pulse beam to the sample by a set amount of time. The outgoing probe beam 20b from the retroreflector 30 is directed downstream from the delay line by mirror 32 and then to mirror 34, which directs the beam onto the sample 22. After reflection or transmission through the sample, the intensity of the probe beam 20 is monitored.

Correct alignment of the incoming probe beam 20a with the retroreflector 30 of the optical delay line 24 is a critical requirement of pump—probe measurement experiments because at any point on the delay line trajectory, pointing of the outgoing probe pulse beam 20a needs to remain the same over the course of the measurements. This is accomplished by properly aligning the incoming beam 20a before it enters the delay line 24. If the incoming beam 20a trajectory is not aligned with a proper axis of the delay stage (and retroreflector), pointing of the outgoing probe pulse beam 20b from the retroreflector will vary as the delay stage (and retroreflector) is translated along the track over the course of the measurements. This will in turn affect the spatial overlap of the pump beam 18 and the probe beam 20 in the sample and result in inaccurate data. However, achieving accurate alignment of the incoming probe beam 20a with the optical delay line is time consuming and requires special technical training.

Alignment of the incoming probe beam 20a with the delay line 24 is currently performed by manually adjusting the steering mirror 26 which directs the probe pulse beam 20 into the delay line. Upon moving the delay stage 28 (and the retroreflector 30) from one end of the track to the other end, and monitoring the position of the outgoing probe pulse beam 20b, for example, using a commercially available beam profiler or position sensitive detector 40 in combination with a beam splitter (mirror) 38, which splits the outgoing probe pulse beam 20b and directs it to the detector 40, or by monitoring the beam position on a target by eye, the angle of the steering mirror 26 is then manually adjusted based on those observations to minimize "walk-off" (i.e., drift) of the outgoing probe beam 20b by ensuring that the incoming beam 20a is aligned and enters the delay line parallel to its axis of translation 36. However, the problem with this approach is that only one mirror 26 can be steered, and a user has no control over the pointing of the outgoing probe pulse beam 20b after the delay line. Consequently, subsequent alignment of the optical set-up (e.g., at least mirrors 32 and 34 and possibly other mirrors) situated "downstream" from the delay line 24 is required after performing each alignment of the delay line.

Figure 2:
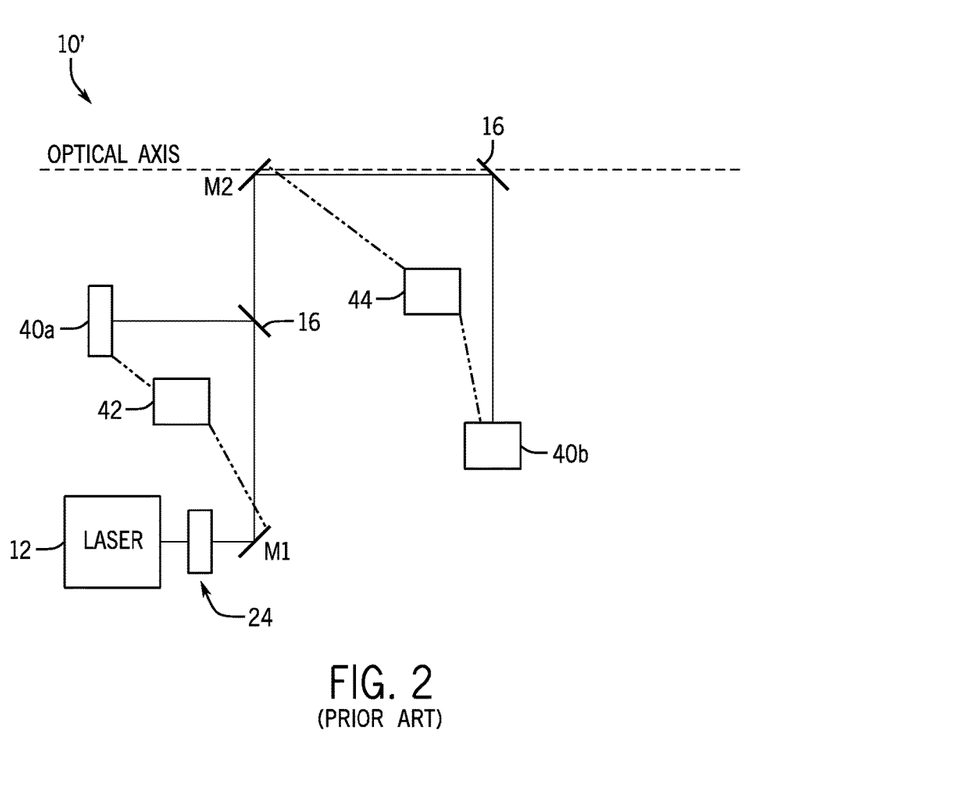
FIG. 2 is a depiction of another embodiment of a conventional system that aligns a beam with a delay line by active beam stabilization.

FIG. 2 illustrates another embodiment of a conventional system 10' that aligns a beam with a delay line by active beam stabilization. Such systems actively compensate for changes in the alignment of outgoing beam from the retroreflector in order to maintain beam pointing along a proper trajectory. In an active beam stabilization system 10', motorized mirrors M1, M2 are controlled through a feedback loop by a closed loop controller 42, 44 connected to a corresponding position sensitive photodetector 40a, 40b. When a beam coordinate moves away from the center of the photodetector 40a, 40b, the motorized steering mirror M1, M2 is activated to compensate for the displacement and bring the beam back on the center of the detector. This is done at high speed to ensure minimum beam displacement caused by changes in the optical set-up (i.e., mirrors M1, M2, etc.). In this method, the distances between the mirror M1, M2 and the photodetector 40a, 40b are not taken into account. The beam stabilization is achieved by simply keeping the beam traveling through the same two points in space.

However, an active beam stabilization approach is unacceptable in a pump-probe experiment because once the delay line scanning starts, the incoming or outgoing beam trajectory cannot be changed. Such an "on the fly" trajectory change will unpredictably affect how much the laser beam gets delayed with changing the position of the retroreflector of the delay line.

Accordingly, there is a need for a set-up and method for aligning a probe beam in relation to a delay line in an optically gated spectroscopy measurement system that will overcome the foregoing problems and retain the initial probe beam pointing after the delay line.

SUMMARY OF THE INVENTION

In embodiments, the invention provides a system for aligning a light beam in a spectroscopic measuring device, the aligning system comprising:

a first motorized mirror positioned to receive and transmit a light beam;

a second motorized mirror positioned relative to the first mirror to receive the light beam from the first mirror and transmit the light beam to a delay line;

a third mirror positioned to receive the light beam from the delay line and transmit said light beam to a detector; and a computer-based processor in communication with the detector and the first and second mirrors, the processor configured to a) receive and process data relating to the light beam from the detector, and b) cause movement of the first and second mirrors to change an angle of the mirrors based on the data relating to the light beam.

In other embodiments, the invention provides a method for aligning a light beam in a spectroscopic measuring device such as a pump-probe device.

DETAILED DESCRIPTION OF THE INVENTION

Various embodiments of the present invention relate to methods for aligning an optical delay line to maintain the initial probe beam pointing after the delay line over the course of a pump-probe measurement process.

Figure 3:
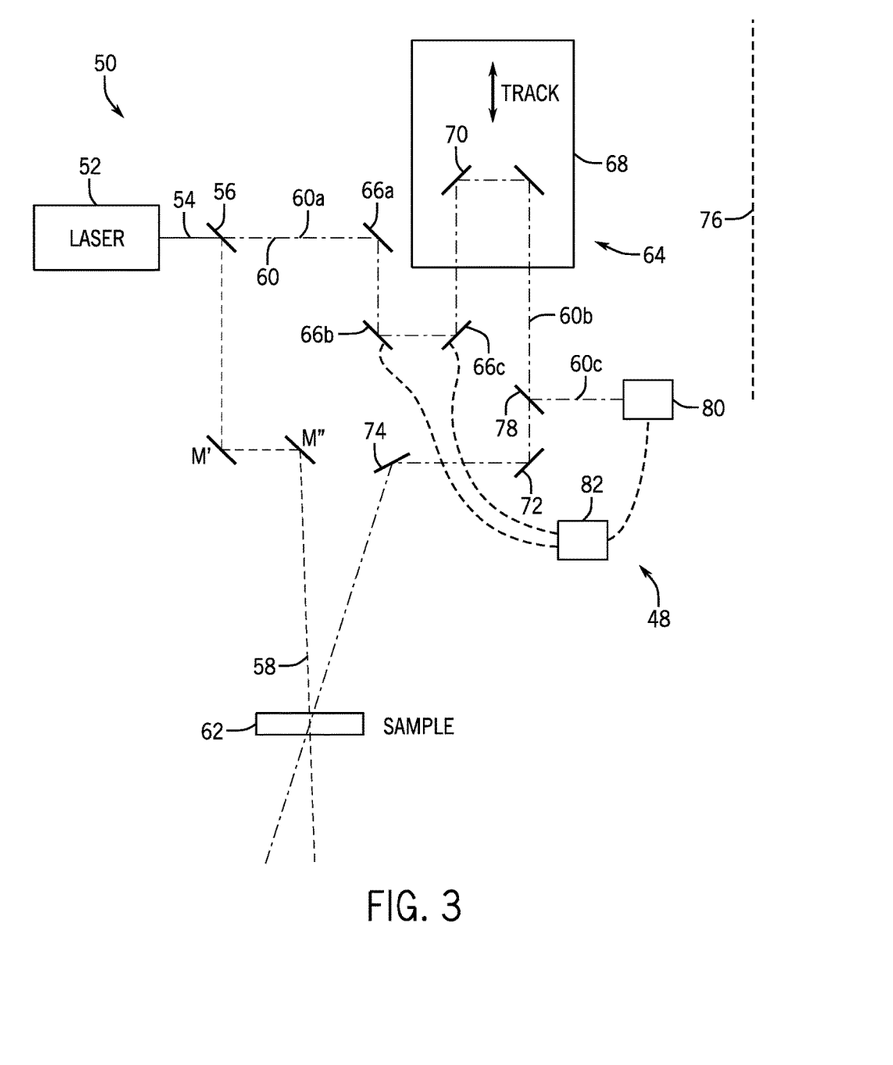
FIG. 3 is a depiction of an embodiment of a beam alignment system according to the invention.

FIG. 3 illustrates an embodiment of a system 50 for aligning a beam according to the invention, incorporated into a pump-probe measurement system.

As illustrated, the pump-probe system 50 includes a laser source 52 which generates a laser beam 54, and a semitransparent beam splitter (mirror) 56 which splits the laser beam 54 into a pump pulse beam 58 and a probe pulse beam 60. The two beams are directed along different optical paths to the sample 62 where the beams 58, 60 spatially overlap. The pump pulse beam 58 is directed via a series of mirrors (e.g., M', M") to the sample 62, and the probe pulse beam 60 is directed to the optical delay line 64 via a series of mirrors (e.g., 66a, 66b, 66c). In some embodiments, the pump pulse beam and the probe pulse beam can be interchanged. For example, a pump pulse beam can directed to the optical delay line via mirrors 66a, 66b, 66c and the probe pulse beam can be directed to the sample (e.g., via mirrors M', M").

The optical delay line 64 includes an optical retroreflector assembly 70 mounted on a computer controlled, motorized linear translation stage 68, which is translated (moved) along a track (arrow ↔). The position of the translation stage 68 (with the retroreflector 70) is varied over the course of the pump-probe measurement period by motorized movement along the track to modify the length of the beam path of the probe pulse beam 60 relative to the length of the pump pulse beam 58, which delays the delivery of the probe pulse beam to the sample by a set time period. In embodiments, the outgoing probe beam 60b from the retroreflector 70 is directed downstream from the delay line by mirror 72 onto mirror 74, which directs the beam onto the sample 62. In the pump-probe measurement process, the intensity of the probe pulse beam 60 after the sample is monitored as a function of the position of the delay line.

The present alignment system 50 provides for the alignment of the outgoing probe pulse beam 60b by maintaining a proper alignment of the incoming probe beam 60a before it enters the delay line 64 to ensure the incoming beam 60a enters the delay line parallel to its axis of translation 76.

In the embodiment of the alignment system 50 illustrated in FIG. 3, the incoming probe pulse beam 60a is steered into the variable (motorized) optical delay line 64 via the beam splitter (mirror) 56 to a mirror 66a, which directs the beam 60a to two computer-controlled, motorized steering mirrors 66b, 66c.

As part of the alignment system 50 a beam splitter (mirror) 78 is positioned in the path of the outgoing probe pulse beam 60b. The beam splitter 78 splits the outgoing probe pulse beam 60b into a beam 60c, and directs the beam 60c to a computer interfaced, position sensitive detector 80 (e.g., a laser beam profiler). Examples of position sensitive detectors include, for example, a 2D camera, a webcam, a quadrant photodetector, or other detecting device. The location of the beam 60c on the detector is recorded as a data point that corresponds to the outgoing beam 60b trajectory and pointing after exiting the optical delay line 64. The position sensitive detector 80 is connected to a computer (or other microprocessor) 82, which is connected to the two motorized steering mirrors 66b, 66c that steer the incoming probe pulse beam 60a into the optical delay line 64.

The alignment system of the invention utilizes a software-based method for aligning the optical delay line 64 while maintaining the pointing of the outgoing probe beam after the delay line.

In an embodiment, the alignment method includes first determining the geometrical model of the system set-up prior to performing the alignment of the delay line. This allows for a minimized alignment time and a quickly converging algorithm. To devise the geometrical model of the system set-up, the approximate distances between the optical elements (i.e., the mirrors, etc.) are determined and recorded (e.g., entered into the software). For example, in the embodiment of the system depicted in FIG. 3, the distances between the following components can be measured and recorded: the distance the beam 60 travels between steering mirrors 66b, 66c, and the distance between mirror 66c and detector 70 for a given position of the delay line 64.

In a next step, with the delay line (i.e., the translation stage 68) set at a first position, the two motorized steering mirrors 66b, 66c are positioned at a set angle, and an incoming probe beam 60a is steered via the mirrors 66b, 66c into the optical delay line 64. The outgoing probe beam 60b exiting the delay line is then intercepted and split by the beam splitter (mirror) 78, which directs beam 60c to the position sensitive detector 80. The location of the beam 60c on the detector 80 is transmitted to the computer 82. Then mirror 66b is moved and repositioned at a computed angle along the vertical axis. The corresponding beam position shift is registered by detector 80 and transferred to the computer. Then mirror 66b is moved and repositioned at a computed angle along the horizontal position. The corresponding beam position shift is registered by detector 80 and transferred to the computer. The same is then done for mirror 66c. This step of repositioning mirrors 66b, 66c at different computed angles is repeated for several delay line positions. That is, the delay line (i.e., translation stage 68) is translated (moved) along the track to a second position. Then mirror 66b is moved at a computed angle along the vertical axis. The corresponding beam position shift is registered by detector 80 and transferred to the computer. Then mirror 66b is moved at a computed angle along the horizontal position. The corresponding beam position shift is registered by detector 80 and transferred to the computer. The same is then done for mirror 66c. The steps of repositioning the delay line and the steering mirrors 66b, 66c, and detecting and recording the outgoing (split) beam 60c are again repeated. Multiple data points of the position of the outgoing (split) beam 60c on the detector 60 are thus acquired and recorded.

The geometrical model of the set-up of the pump-probe device is then determined by processing the acquired data points (e.g., by the computer 82). The model data are saved and used to calculate desired angular adjustments of the steering mirrors 66b, 66c to ensure correct beam pointing and delay line alignment. The adjustments to the steering mirrors 66b, 66c can be verified by the computer (e.g., software) by translating the delay line 64 over the length of the track and recording the position of the outgoing (split) beam 60c on the position sensitive detector 80. If the measured beam displacement is still too large, the procedure can undergo a additional iterations until the desired beam displacement is achieved.

The present alignment system and method provide for correct alignment of the incoming probe beam with the retroreflector of the optical delay line, resulting in the predetermined pointing of the outgoing probe pulse beam remaining constant over the course of the probe-pump measurements. This ensures the correct spatial overlap of the pump pulse beam and the probe pulse beam in the sample and accurate data measurements of the sample.

Calibration

Figure 4:
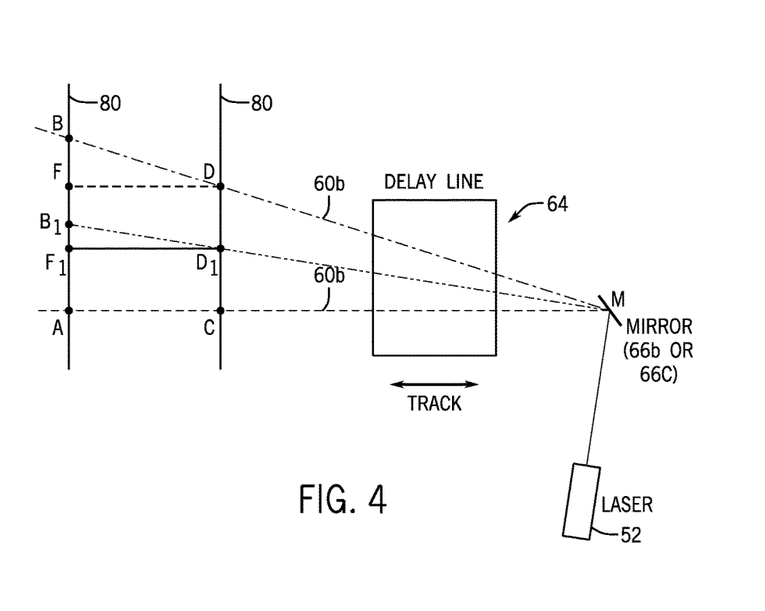
FIG. 4 is a depiction of an embodiment of a calibration process to determine the geometrical model of a measuring system.

FIG. 4 illustrates a calibration principle of each of the motorized steering mirrors 66b, 66c (shown in FIG. 3), that is, a determination (calculation) of the geometrical model of the pump-probe system incorporating the alignment elements according to the invention.

The position of the retroreflector 70 on the optical delay line 64 dictates the distance the light has to travel between mirror M (66b or 66c) and the position sensitive detector 80. Therefore, by moving the delay line, the plane of the position sensitive detector 80 is effectively positioned closer or farther away from mirror M (66b or 66c), which is illustrated in FIG. 4.

The position sensitive detector 80, which remains stationary, is situated in a plane AB or plane CD, depending on the position of the delay line 64, which translates (moves) along the track (arrow ↔). By controlling the position of the delay line 64 along the track, the plane of the detector 80 can be shifted arbitrarily with respect to the mirror M (e.g., 66b, 66c).

In an embodiment of the method of the invention, a calibration to determine the geometrical model of the pump-probe system 50 (FIG. 3) is conducted. The calibration is then used to establish a relation between the rotation angle (angle A-M-B) of the mirror M (66b, 66c) and the displacement of the laser beam on the detector 80 in plane AB or plane CD, depending on the position of the delay line 64. Upon establishing this relation, the software can predict to what angle a mirror (66b, 66c) needs to be turned in order for the beam to be incident at a particular point on the detector 80 for a certain position of the delay line 64 (distance of the detector 80 from the mirror (66b, 66c) that is being turned).

Alignment

In embodiments of the present methods, upon conducting the calibration and determining the geometrical model of the pump-probe system 50 (incorporating the alignment elements), the delay line position and the rotation angles for each mirror (66b, 66c) required for sending the beam through any two accessible points in space after the delay line 64 are then determined.

Figure 5:
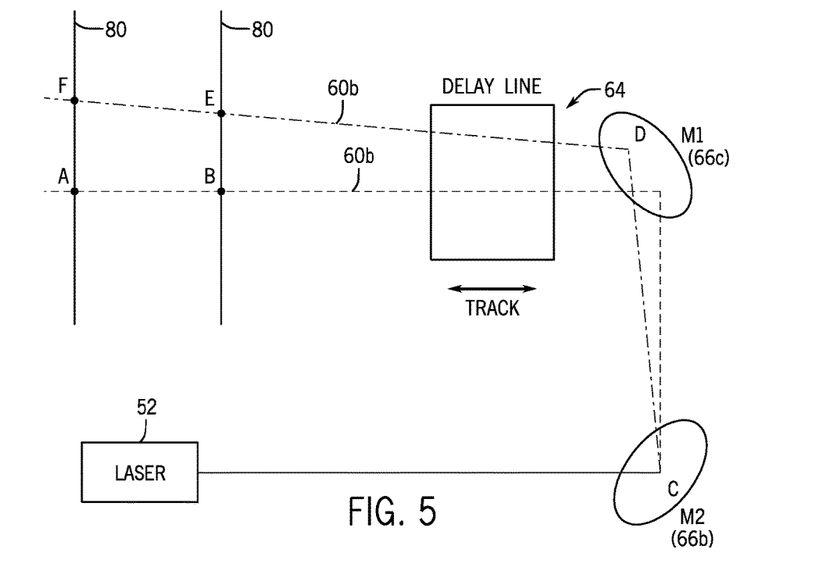
FIG. 5 is a depiction of an embodiment of an alignment process for a delay line and mirrors of a measuring system.

A general objective toward aligning a pump-probe spectrometer is to position the beam (e.g., outgoing beam 60b, FIG. 3) so that the beam travels through points A and B as the desired optical axis, as depicted in FIG. 5. Points A and B correspond to the same position on the detector 80, which means the beam does not shift on the detector as the position of the delay line 64 is changed.

By example, in a set-up in which the steering mirrors (66b, 66c) and the delay line 64 are misaligned, the beam (e.g., outgoing beam 60b, FIG. 3) can travel along trajectory that is not the desired optical axis (A-B), such as trajectory C-D-E-F shown in FIG. 5. Having performed the calibration procedure for mirrors M1 and M2 (66b, 66c), the angle at which each of these mirrors must be turned in order for the beam to simultaneously hit any of the two pairs of points A and B or E and F has been determined.

Thus, in one embodiment, in a first step (1), the computer (software) signals mirror M1 (e.g., 66c) to rotate to the computed angle to send the beam along a straight line from point D to point A. In a second step (2), the computer (software) signals mirror M2 (e.g., 66b) to turn to a computed angle to send the beam from point C bouncing off mirror M1 (e.g., 66c) to point B. However, by doing so the beam will now be missing point A by a predictable distance. Steps 1 and 2 can then be repeated to achieve the desired accuracy of beam pointing.

In another embodiment, based on the geometrical model of the setup, the computer (software) can pre-calculate the degree to which the mirror M1 (e.g., 66c) should rotate in order to overshoot point A to compensate for the subsequent rotation of mirror M2 (e.g., 66b). In such an embodiment, in a first step (1), the computer (software) then signals to rotate mirror M1 (e.g., 66c) to a computed angle such that the beam overshoots point A just enough to compensate for the subsequent rotation of mirror M2 (e.g., 66b). In a second step, the computer (software) signals mirror M2 (e.g., 66b) to turn to a computed angle which directs the beam to M1 (e.g., 66c) and then exactly to point A. Since mirror M1 (e.g., 66c) is placed in correct position in step one (1), the beam will then go exactly through points B and A. To compensate for instrument errors related to the accuracy of the mirror rotation, etc., steps 1 and 2 can be repeated as necessary to achieve the desired accuracy of beam pointing.

In other embodiments, alternative orders for mirror rotation can be utilized and detector feedback can be used where necessary.

It should be appreciated that the present invention is intended to encompass numerous embodiments. For example, in embodiments, the invention relates to system for aligning a light beam in a spectroscopic measuring device, the aligning system comprising: a first motorized mirror positioned to receive and transmit a light beam; a second motorized mirror positioned relative to the first mirror to receive the light beam from the first mirror and transmit the light beam to a delay line; a third mirror positioned to receive the light beam from the delay line and transmit said light beam to a detector; a computer-based processor in communication with the detector and the first and second mirrors, the processor configured to a) receive and process data relating to the light beam from the detector, and b) cause movement of the first and second mirrors to change an angle of the mirrors based on the data relating to the light beam.

In another embodiment, the invention relates to a method for aligning a light beam in a spectroscopic measuring device, the method comprising: a) Optionally, determining distances between optical components of an alignment system, the optical components comprising first and second motorized mirrors for transmitting the light beam to a delay line, a detector, and a third mirror for transmitting the light beam to the detector; b) With the delay line in a first position and each of the first and second mirrors set at a first angle, conducting a light beam to the delay line via the first and second mirrors such that the light beam exiting the delay line is transmitted to the detector via the third mirror; c) Transmitting a first location of the beam on the detector to a computer-based processor; d) Establishing a relationship between the angle of the first mirror and the position of the beam on the detector; e) Establishing a relationship between the angle of the second mirror and the position of the beam on the detector; and f) Establishing a relationship between the position of the delay line and the position of the beam on the detector. In an embodiment, the method further comprises verifying the beam alignment of the beam by registering the beam position on the detector at different positions of the delay line.

In an embodiment, after step f), the method further comprises a step g) Determining how the beam position on the detector depends on the angles of the first and second mirrors and the position of the delay line. In an embodiment, determining how the beam position 60b on the detector 80 depends on the angles of the first and second mirrors, M1 (e.g., 66c) and M2 (e.g., 66b) and the position of the delay line 64. In an embodiment, a determination of this relationship involves calculating all sides and angles of triangle C-D-M, illustrated in FIG. 4. In an embodiment, the calculation can be conducted by measuring the distance C-M between the detector 80 and the mirror M (e.g., 66b or 66c) (e.g., using a ruler). Moving the delay line 64 by a distance F-D will result in a shift of the beam 60b on the detector 80 by a distance B-F. Angle B-F-D is known (e.g., 90°), which allows the calculation of angle F-D-B, which is the same as angle C-M-D. Angle D-C-M is known (e.g., 90°), which allows one to calculate all sides and angles of triangle C-D-M.

In another embodiment, the step g) of determining the relationship of the beam position on the detector 80 with the angles of the mirrors (e.g., 66b, 66c) and the position of the delay line 64 can be conducted by pointing the beam 60b from mirror M (e.g., 66b or 66c) towards point D of the detector 80. The delay line 64 can then be moved by a distance D-F to translate the detector 80 from plane C-D to plane A-B and register the beam shift distance B-F. Then, mirror M can be rotated to send the beam 60b to point B1 on the detector 80 and register the shift of the beam position B-B1. Then, delay line 64 can be moved back to bring the detector 80 back to plane C-D and register the beam shift distance B1-F1. Angles B-F-D and B1-F1-D1 are known (e.g., 90°), which allows the calculation of all sides and angles of triangles B-D-F and B1-D1-F1. This calculation then allows the calculation of all sides and angles of triangle D-D1-M. With the distance D1-M known, angle D1-C-M (e.g., 90°) and angle C-D1-M (e.g., 180° minus D-D1-M), one can calculate all sides and angles of triangle D1-C-M. Now, knowing all sides and angles of triangles D-D1-M and D1-C-M, one can easily calculate all sides and angles of triangle C-D-M. Other methods of calculating all sides and angles of triangle C-D-M can be used.

In an embodiment, after step g), the method further comprises a step h) Adjusting the angles of the first and second mirrors to transmit the beam to a desired position on the detector. In an embodiment, steps d) and e) of establishing a relationship between the angle of the first and second mirrors and the position of the beam on the detector comprises: (1) Moving the first or second mirror at a first angle along a vertical axis to transmit the beam to the detector, registering a location of the beam on the detector, and transmitting said beam location to the computer-based processor; (2) Moving the mirror of step (1) at a second angle along a horizontal axis to transmit the beam to the detector, registering a location of the beam on the detector and transmitting said beam location to the computer-based processor, and (3) Repeating steps (1) and (2) for the other of the first and second mirrors. In an embodiment, step f) of establishing a relationship between the position of the delay line and the position of the beam on the detector comprises: (1) Moving the delay line to a second position; (2) Moving the first or second mirror at a first angle along a vertical axis to transmit the beam to the detector, registering a location of the beam on the detector, and transmitting said beam location to the computer-based processor; (3) Moving the mirror of step (2) at a second angle along a horizontal axis to transmit the beam to the detector, registering a location of the beam on the detector, and transmitting said beam location to the computer-based processor; and (4) Repeating steps (2) and (3) for the other of the first and second mirrors. In an embodiment, after step (4), the method further comprises a step (5) Moving the delay line to a third position and repeating steps (2) through (4). In an embodiment, after step (5), the method further comprises a step (6) Determining how the beam position on the detector depends on the angles of the first and second mirrors and the position of the delay line. In an embodiment, step f) of establishing a relationship between the position of the delay line and the position of the beam on the detector comprises: (1) Moving the delay line to a second position, and a) Moving the first mirror at a first angle along a vertical axis to transmit the beam to the detector, registering a location of the beam on the detector, and transmitting said beam location to the computer-based processor; b) Moving the first mirror at a second angle along a horizontal axis to transmit the beam to the detector, registering a location of the beam on the detector, and transmitting said beam location to the computer-based processor; c) Moving the second mirror at a first angle along a vertical axis to transmit the beam to the detector, registering a location of the beam on the detector, and transmitting said beam location to the computer-based processor; d) Moving the second mirror at a second angle along a horizontal axis to transmit the beam to the detector, registering a location of the beam on the detector, and transmitting said beam location to the computer-based processor; (2) Moving the delay line to a third position and repeating steps (1a) through (1d);

and (3) Determining how the beam position on the detector depends on the angles of the first and second mirrors and the position of the delay line.

In another embodiment, the invention relates to a method for aligning a light beam in a spectroscopic measuring device, the method comprising: a) Optionally, determining distances between optical components of an alignment system, the optical components comprising first and second motorized mirrors for transmitting the light beam to a delay line, a detector, and a third mirror for transmitting the light beam to the detector; b) With the delay line in a first position and each of the first and second mirrors set at a first angle, conducting a light beam to the delay line via the first and second mirrors such that the light beam exiting the delay line is transmitted to the detector via the third mirror; c) Transmitting a first location of the beam on the detector to a computer-based processor; d) Establishing a relationship between the angle of the first mirror and the position of the beam on the detector: (1) moving the first mirror at a first angle along a vertical axis; (2) registering a second location of the beam on the detector and transmitting said second beam location to the computer-based processor; (3) moving the first mirror at a second angle along a horizontal axis; and (4) registering a third location of the beam on the detector and transmitting said third beam location to the computer-based processor; e) Establishing a relationship between the angle of the second mirror and the position of the beam on the detector: (1) moving the second mirror at a first angle along a vertical axis; (2) registering a fourth location of the beam on the detector and transmitting said fourth beam location to the computer-based processor; (3) moving the second mirror at a second angle along a horizontal axis; and (4) registering a fifth location of the beam on the detector and transmitting said fifth beam location to the computer-based processor; f) Establishing a relationship between the position of the delay line and the position of the beam on the detector: (1) moving the delay line to a second position; and (1a) moving the first mirror at a first angle along a vertical axis;(1b) registering a sixth location of the beam on the detector and transmitting said sixth beam location to the computer-based processor; (1c) moving the first mirror at a second angle along a horizontal axis; and (1d) registering a seventh location of the beam on the detector and transmitting said seventh beam location to the computer-based processor; (1e) moving the second mirror at a first angle along a vertical axis;(1f) registering a eight location of the beam on the detector and transmitting said eighth beam location to the computer-based processor; (1g) moving the second mirror at a second angle along a horizontal axis; and (1h) registering a ninth location of the beam on the detector and transmitting said ninth beam location to the computer-based processor; and (2) moving the delay line to a third position and repeating steps (1a) through (1h); g) Processing the beam position changes on the detector to correspond the changes in angles of the first and second mirrors with the position of the delay line; and h) Adjusting the angles of the first and second mirrors to send the beam to a desired position on the detector.

In another embodiment, the invention relates to a method for aligning a light beam in a spectroscopic measuring device, the device comprising an alignment system, and the method comprising: optionally, determining distances between optical components of the alignment system, the optical components comprising first and second motorized mirrors, a third mirror, and a detector; transmitting a light beam from a first mirror to a second mirror and then through a delay line situated in a first position to a detector, and recording a location of the light beam on the detector; recording the locations of the light beam on the detector after altering an angle of the first mirror , and after altering an angle of the second mirror; moving the delay line to a second position and to a third position, and at each of the second and third positions of the delay line, recording the locations of the light beam on the detector after altering an angle of the first mirror, and after altering an angle of the second mirror; processing the beam position changes on the detector to correspond the changes in angles of the first and second mirrors with the position of the delay line; and adjusting the angles of the first and second mirrors to send the beam to a desired position on the detector. In an embodiment of the method, the angles of the mirrors are altered along at least one of a vertical axis and a horizontal axis, and the locations of the light beam are recorded for each of the angles along said vertical axis and said horizontal axis. In an embodiment, the angles of the mirrors are altered along both a vertical axis and a horizontal axis.

In another embodiment, the invention relates to a method for aligning a light beam in a spectroscopic measuring device, the device comprising an alignment system, and the method comprising: optionally, determining distances between optical components of the alignment system, the optical components comprising first and second motorized mirrors, a third mirror, and a detector; transmitting a light beam from a first mirror to a second mirror and then through a delay line situated in a first position to a detector, and recording a location of the light beam on the detector; recording the locations of the light beam on the detector after altering an angle of the first mirror; recording the locations of the light beam on the detector after altering an angle of the second mirror; moving the delay line to a second position, and recording the locations of the light beam on the detector after altering an angle of the first mirror, and after altering an angle of the second mirror; moving the delay line to a third position, and recording the locations of the light beam on the detector after altering an angle of the first mirror, and after altering an angle of the second mirror; processing the beam position changes on the detector to correspond the changes in angles of the first and second mirrors with the position of the delay line; and adjusting the angles of the first and second mirrors to send the beam to a desired position on the detector. In an embodiment of the method, the angles of the mirrors are altered along at least one of a vertical axis and a horizontal axis, and the locations of the light beam are recorded for each of the angles along said vertical axis and said horizontal axis.

It is specifically intended that the present invention not be limited to the embodiments and illustrations contained herein, but include modified forms of those embodiments including portions of the embodiments and combinations of elements of different embodiments as come within the scope of the following claims.

What is claimed:

1. A method for aligning a light beam in a spectroscopic measuring device, the method comprising:
   a) providing an a system comprising optical components comprising first and second motorized mirrors for transmitting the light beam to a delay line, a detector, and a third mirror for transmitting the light beam to the detector;
   b) With the delay line in a first position and each of the first and second mirrors set at a first angle, conducting a light beam to the delay line via the first and second mirrors such that the light beam exiting the delay line is transmitted to the detector via the third mirror;

c) Transmitting a first location of the beam on the detector to a computer-based processor;
d) Establishing a relationship between the angle of the first mirror and the position of the beam on the detector;
e) Establishing a relationship between the angle of the second mirror and the position of the beam on the detector; and
f) Establishing a relationship between the position of the delay line and the position of the beam on the detector;
wherein the steps d) and e) of establishing a relationship between the angle of the first and second mirrors and the position of the beam on the detector comprises:
(1) Moving the first or second mirror at a first angle along a vertical axis to transmit the beam to the detector, registering a location of the beam on the detector, and transmitting said beam location to the computer-based processor;
(2) Moving the mirror of step (1) at a second angle along a horizontal axis to transmit the beam to the detector, registering location of the beam on the detector and transmitting said beam location to the computer-based processor; and
(3) Repeating steps (1) and (2) for the other of the first and second mirrors.

2. The method of claim 1, further comprising verifying the beam alignment of the beam by registering the beam position on the detector at different positions of the delay line.

3. The method of claim 1, after step f), further comprising:
g) Determining how the beam position on the detector depends on the angles of the first and second mirrors and the position of the delay line.

4. The method of claim 3, after step g), further comprising:
h) Adjusting the angles of the first and second mirrors to transmit the beam to a desired position on the detector.

5. The method of claim 1, wherein the step f) of establishing relationship between the position of the delay line and the position of the beam on the detector comprises:
(1) Moving the delay line to a second position; and
(2) Moving the first or second mirror at a first angle along a vertical axis to transmit the beam to the detector, registering a location of the beam on the detector, and transmitting said beam location to the computer-based processor;
(3) Moving the mirror of step (2) at a second angle along a horizontal axis to transmit the beam to the detector, registering a location of the beam on the detector, and transmitting said beam location to the computer-based processor; and
(4) Repeating steps (2) and (3) for the other of the first and second mirrors.

6. The method of claim 5, further comprising after step (4):
(5) Moving the delay line to a third position and repeating steps (2) through (4).

7. The method of claim 6, further comprising after step (5):
(6) Determining how the beam position on the detector depends on the angles of the first and second mirrors and the position of the delay line.

8. A method for aligning a light beam in a spectroscopic measuring device, the method comprising:
a) providing alignment system comprising optical components comprising first and second motorized mirrors for transmitting the light beam to a delay line, a detector, and a third mirror for transmitting the light beam to the detectors;
b) With the delay line in a first position and each of the first and second mirrors set at a first angle, conducting a light beam to the delay line via the first and second mirrors such that the light beam exiting the delay line is transmitted to the detector via the third mirror;
c) Transmitting a first location of the beam on the detector to a computer-based processor;
d) Establishing a relationship between the angle of the first mirror and the position of the beam on the detector;
e) Establishing a relationship between the angle of the second mirror and the position of the beam on the detector; and
f) Establishing a relationship between the position of the delay line and the position of the beam on the detector, comprising
(1) Moving the delay line to a second position, and
a) Moving the first mirror at a first angle along a vertical axis to transmit the beam to the detector, registering a location of the beam on the detector, and transmitting said beam location to the computer-based processor;
b) Moving the first mirror at a second angle along a horizontal axis to transmit the beam to the detector, registering a location of the beam on the detector, and transmitting said beam location to the computer-based processor;
c) Moving the second mirror at a first angle along a vertical axis to transmit the beam to the detector, registering a location of the beam on the detector, and transmitting said beam location to the computer-based processor;
d) Moving the second mirror at a second angle along a horizontal axis to transmit the beam to the detector, registering a location of the beam on the detector, and transmitting said be location to the computer-based processor;
(2) Moving the delay line to a third position and repeating steps (1a) through (1d); and
(3) Determining how the beam position on the detector depends on the angles of the first and second mirrors and the position of the delay line.

9. A method for aligning a light beam in a spectroscopic measuring device, the method comprising:
a) providing an alignment system comprising optical components comprising first and second motorized mirrors for transmitting the light beam to a delay line, a detector, and a third mirror for transmitting the light beam to the detector;
b) With the delay line in a first position and each of the first and second mirrors set at a first angle, conducting a light beam to the delay line via the first and second mirrors such that the light beam exiting the delay line is transmitted to the detector via the third mirror;
c) Transmitting a first location of the beam on the detector to a computer-based processor;
d) Establishing a relationship between the angle of the first mirror and the position of the beam on the detector:
(1) moving the first mirror at a first angle along a vertical axis;
(2) registering a second location of the beam on the detector and transmitting said second beam location to the computer-based processor;
(3) moving the first mirror at a second angle along a horizontal axis; and
(4) registering a third location of the beam on the detector and transmitting said third beam location to the computer-based processor;

e) Establishing a relationship between the angle of the second mirror and the position of the beam on the detector:
   (1) moving the second mirror at a first angle along a vertical axis;
   (2) registering a fourth location of the beam on the detector and transmitting said fourth beam location to the computer-based processor;
   (3) moving the second mirror at a second angle along a horizontal axis; and
   (4) registering a fifth location of the beam on the detector and transmitting said fifth beam location to the computer-based processor;
f) Establishing a relationship between the position of the delay line and the position of the beam on the detector:
   (1) moving the delay line to a second position; and
      (1a) moving the first mirror at a first angle along a vertical axis;
      (1b) registering a sixth location of the beam on the detector and transmitting said sixth beam location to the computer-based processor;
      (1c) moving the first mirror at a second angle along a horizontal axis; and
      (1d) registering a seventh location of the beam on the detector and transmitting said seventh beam location to the computer-based processor;
      (1e) moving the second mirror at a first angle along a vertical axis;
      (1f) registering a eight location of the beam on the detector and transmitting said eighth beam location to the computer-based processor;
      (1g) moving the second mirror at a second angle along a horizontal axis; and
      (1h) registering a ninth location of the beam on the detector and transmitting said ninth beam location to the computer-based processor; and
   (2) moving the delay line to a third position and repeating steps (1a) through (1h);
g) Processing the beam position changes on the detector to correspond the changes in angles of the first and second mirrors with the position of the delay line; and
h) Adjusting the angles of the first and second mirrors to send the beam to a desired position on the detector.

10. A method for aligning a light beam in a spectroscopic measuring device, the device comprising an alignment system, and the method comprising:
   transmitting a light beam from a first mirror to a second mirror and then through a delay line situated in a first position to a detector, and recording a location of the light beam on the detector;
   recording the locations of the light beam on the detector after altering an angle of the first mirror, and after altering an angle of the second mirror; and
   moving the delay line to a second position and to a third position, and at each of the second and third positions of the delay line, recording the locations of the light beam on the detector after altering an angle of the first mirror, and after altering an angle of the second mirror;
   processing the beam position changes on the detector to correspond the changes in angles of the first and second mirrors with the position of the delay line; and
   adjusting the angles of the first and second mirrors to send the beam to a desired position on the detector.

11. The method of claim 10, wherein the angles of the mirrors are altered along at least one of a vertical axis and a horizontal axis, and the locations of the light beam are recorded for each of the angles along said vertical axis and said horizontal axis.

12. The method of claim 11, wherein the angles of the mirrors are altered along both a vertical axis and a horizontal axis.

13. A method for aligning a light beam in a spectroscopic measuring device, the device comprising an alignment system, and the method comprising:
   transmitting a light beam from a first mirror to a second mirror and then through a delay line situated in a first position to a detector, and recording location of the light beam on the detector;
   recording the locations of the light beam on the detector after altering an angle of the first mirror;
   recording the locations of the light beam on the detector after altering an angle of the second mirror;
   moving the delay line to a second position, and recording the locations of the light beam on the detector after altering an angle of the first mirror, and after altering an angle of the second mirror;
   moving the delay line to a third position, and recording the locations of the light beam on the detector after altering an angle of the first mirror, and after altering an angle of the second mirror;
   processing the beam position changes on the detector to correspond the changes in angles of the first and second mirrors with the position of the delay line; and
   adjusting the angles of the first and second mirrors to send the beam to a desired position on the detector.

14. The method of claim 13, wherein the angles of the mirrors are altered along at least one of a vertical axis and a horizontal axis, and the locations of the light beam are recorded for each of the angles along said vertical axis and said horizontal axis.

* * * * *

UNITED STATES PATENT AND TRADEMARK OFFICE
CERTIFICATE OF CORRECTION

PATENT NO. : 10,209,131 B2
APPLICATION NO. : 15/753459
DATED : February 19, 2019
INVENTOR(S) : Alexander Sobolev, Nikita Kurakin and Alexey Gusev Page 1 of 1

It is certified that error appears in the above-identified patent and that said Letters Patent is hereby corrected as shown below:

In the Claims

Column 10, Line 58 Claim 1; Change "an a system" to --an alignment system--

Column 11, Line 20 Claim 1; Change "registering location" to --registering a location--

Column 11, Line 63 Claim 8; Change "providing alignment" to --providing an alignment--

Column 11, Line 67 Claim 8; Change "detectors" to --detector--

Column 12, Line 35 Claim 8; Change "be" to --beam--

Column 14, Line 26 Claim 13; Change "recording location" to --recording a location--

Signed and Sealed this
Fourth Day of June, 2019

Andrei Iancu
*Director of the United States Patent and Trademark Office*